United States Patent
Rollat-Corvol et al.

(10) Patent No.: US 7,740,832 B1
(45) Date of Patent: *Jun. 22, 2010

(54) COSMETIC COMPOSITION COMPRISING AT LEAST A TACKY POLYMER AND AT LEAST A FIXING POLYMER

(75) Inventors: Isabelle Rollat-Corvol, Boulogne-Billancourt (FR); Henri Samain, Bièvres (FR)

(73) Assignee: L'Oreal S.A., Paris (FR)

( * ) Notice: Subject to any disclaimer, the term of this patent is extended or adjusted under 35 U.S.C. 154(b) by 798 days.

This patent is subject to a terminal disclaimer.

(21) Appl. No.: 09/719,101

(22) PCT Filed: Jun. 8, 1999

(86) PCT No.: PCT/FR99/01347

§ 371 (c)(1),
(2), (4) Date: Feb. 23, 2001

(87) PCT Pub. No.: WO99/63955

PCT Pub. Date: Dec. 16, 1999

(30) Foreign Application Priority Data

Jun. 11, 1998 (FR) .................................. 98 07376

(51) Int. Cl.
*A61K 8/72* (2006.01)
*A61K 8/73* (2006.01)
*A61K 8/81* (2006.01)
*A61K 9/12* (2006.01)
*A61K 9/00* (2006.01)

(52) U.S. Cl. .................. 424/70.11; 424/70.13; 424/47; 424/45; 424/70.16

(58) Field of Classification Search .............. 424/70.13, 424/47, 70.11, 45, 70.16
See application file for complete search history.

(56) References Cited

U.S. PATENT DOCUMENTS

| 4,007,147 A | | 2/1977 | Leeson et al. | |
|---|---|---|---|---|
| 4,402,977 A | * | 9/1983 | Grollier et al. | ........... 424/70.13 |
| 5,234,627 A | | 8/1993 | Damschroder | |
| 5,266,303 A | | 11/1993 | Myers et al. | |
| 5,441,728 A | | 8/1995 | Tsaur et al. | |
| 6,346,234 B1 | * | 2/2002 | Rollat et al. | .................. 424/47 |

FOREIGN PATENT DOCUMENTS

| EP | 0 524 346 | | 1/1993 |
|---|---|---|---|
| EP | 0 551 749 | | 7/1993 |
| EP | 0 764 436 | A1 | 3/1997 |
| EP | 0 737 233 | B1 | 2/1998 |
| JP | H07-145023 | | 6/1995 |
| WO | WO 95/00105 | | 1/1995 |
| WO | WO 95/18191 | | 7/1995 |
| WO | WO 95/33437 | | 12/1995 |
| WO | WO 97/08261 | | 3/1997 |
| WO | WO 97/20899 | | 6/1997 |

* cited by examiner

*Primary Examiner*—Shengjun Wang
(74) *Attorney, Agent, or Firm*—Finnegan, Henderson, Farabow, Garrett & Dunner, L.L.P.

(57) ABSTRACT

The invention concerns a cosmetic composition for keratinous fibers such as hair comprising, in a cosmetically acceptable medium, at least a tacky polymer with glass transition temperature (Tg) less than 20° C. and at least a fixing polymer with glass transition temperature higher than 15° C. The invention also concerns a method for treating keratinous fibers such as hair, in particular a method for setting and/or maintaining hairstyle, using said composition and the use of said composition in or for making a cosmetic hairstyling formulation.

69 Claims, No Drawings

COSMETIC COMPOSITION COMPRISING AT LEAST A TACKY POLYMER AND AT LEAST A FIXING POLYMER

The subject of the invention is a cosmetic composition for keratinous fibres such as the hair comprising, in a cosmetically acceptable medium, at least one tacky polymer having a glass transition temperature of less than 20° C. and at least one fixing polymer having a glass transition temperature greater than 15° C. It also relates to a method of treating keratinous fibres such as hair, in particular a method of fixing and/or maintaining hairstyle, using the said composition as well as the use of this composition in or for making a cosmetic hairstyling formulation.

For the purposes of the present invention, the expression "keratinous fibres" is understood to mean the hair, the eyelashes and the eyebrows and the expression "tacky polymer" a polymer which, after application by pressing onto an identical polymer, resists an attempt at separation.

The fixing of the hairstyle is an important component of hairstyling which consists in maintaining the shape already made or in shaping the hair and in fixing it simultaneously. The expression "fixing polymer" is understood to mean a polymer which maintains the shape of the hair or which makes it possible to shape the hair and to fix it simultaneously.

The hair products for shaping and/or maintaining the hairstyle which are most common on the cosmetics market are compositions to be sprayed, essentially consisting of a solution, most often an alcohol or aqueous solution, and one or more materials, generally polymeric resins, whose function is to form bonds between the hair, also called fixing materials, in the form of a mixture with various cosmetic adjuvants. This solution is generally packaged either in an appropriate aerosol container pressurized with the aid of a propellant, or in a pump dispenser.

Hairstyling gels or foams are also known which are generally applied to wet hair before blow-drying or hair setting. Unlike conventional aerosol lacquers, these compositions have the disadvantage of not allowing the fixing of hair in a shape which already exists. Indeed, these compositions are essentially aqueous and their application wets the hair and cannot therefore maintain the initial shape of the hairstyle. To shape and fix the hairstyle, it is therefore necessary to then carry out blow-drying or drying.

Most of the compositions of the state of the art have the same disadvantage of not fixing or maintaining the hairstyle for a sufficiently long period. Thus, the shape initially given to the hairstyle gradually disappears during the day, this in fact happening more quickly if the person is moving about. Consequently, it is often necessary to repeat all the hairstyling and fixing operations if it is desired to recover the initial hairstyle.

Hairstyling compositions are therefore being sought which offer a sufficiently strong fixing and maintaining effect for the hairstyle to suitably withstand the various stresses over time.

Finally, the compositions intended for fixing the hairstyle sometimes have the disadvantage of impairing the cosmetic properties of the hair. Thus, the hair may become rough, difficult to disentangle, lose its pleasant feel and appearance. Hairstyling compositions are therefore being sought which offer good cosmetic properties, in particular in terms of disentanglement, softness and feel.

A need therefore exists to find cosmetic compositions, in particular for hairstyling, which do not have the set of disadvantages indicated above.

Surprisingly and unexpectedly, the Applicant has discovered that when tacky polymers, in particular branched sulphonic polyesters or (meth)acrylic ester polymers, are combined with certain fixing polymers, it is possible to obtain cosmetic compositions which meet the requirements expressed above.

The subject of the invention is therefore a cosmetic composition for keratinous fibres such as the hair comprising, in a cosmetically acceptable medium, at least one tacky polymer having a glass transition temperature (Tg) of less than 20° C. and at least one fixing polymer having a glass transition temperature (Tg) greater than 15° C.

Advantageously, a tacky polymer is chosen which has a peeling profile defined by at least one maximum peeling force $F_{max}$>3 Newton, and preferably greater than 5 N.

More advantageously still, the peeling profile is defined, in addition, by an energy for separation $E_{s(M/V)}$ of the material brought into contact with a glass surface of less than 300 µJ, when the glass transition temperature of the tacky polymer is less than −15° C.

The maximum peeling force $F_{max}$ is the maximum tensile force, measured with the aid of an extensometer, necessary to peel apart the respective 38 mm² surfaces of two rigid, inert and nonabsorbent supports (A) and (B) placed opposite each other; the said surfaces being previously coated with the tacky polymer previously dissolved at 5% in an aqueous, aqueous-alcoholic or alcoholic solvent, at the rate of 1 mg/mm², dried for 24 hours at 22° C. under a relative humidity of 50%, then subjected for 20 seconds to a compression of 3 Newton and finally subjected for 30 seconds to pulling at the rate of 20 mm/min.

Advantageously, supports (A) and (B) consisting of polyethylene, polypropylene, metal alloy or glass are used.

The separation energy $E_{s(M/V)}$ is the energy provided by the extensometer in order to carry out the separation of the respective 38 mm² surfaces of two rigid, inert and nonabsorbent supports (C) and (D) placed opposite each other; one of the said supports consisting of cut glass and the other of the said supports being of an identical nature to the supports (A) and (B) as defined in claim 4 or 5 and whose surface is previously coated with the tacky polymer previously dissolved at 5% in an aqueous, aqueous-alcoholic or alcoholic solvent, at the rate of 1 mg/mm², dried for 24 hours at 22° C. under a relative humidity of 50%, the two surfaces of the said supports (C) and (D) being subjected for 20 seconds to a compression of 0.3 Newton and finally subjected for 30 seconds to pulling at the rate of 20 mm/min.

The separation energy $E_{s(M/V)}$ is work which can be calculated by means of the following formula:

$$\int_{X_{s1}+0.05}^{X_{s2}} F(x)\,dx$$

where F(x) is the force necessary to produce a movement (x);

$x_{s1}$ is the movement (expressed in millimeters) produced by the maximum tensile force;

$x_{s2}$ is the movement (expressed in millimeters) produced by the tensile force which allows the complete separation of the two surfaces of the supports (C) and (D).

Preferably, a tacky polymer will be chosen such that the maximum peeling force $F_{max}$ is greater than 5 Newton and/or such that its glass transition temperature (Tg) is less than 20° C. If the Tg of the polymer is less than −15° C., it will preferably need to have in addition a separation energy $E_{s(M/V)}$ of less than 300 µJ.

The relative concentration by weight of tacky polymer in the composition is in general greater than 0.01%, more preferably greater than 0.1%, and more preferably still greater than 0.5%.

According to a first advantageous embodiment of the present invention, a branched sulphonic polymer or (meth) acrylic ester polymers are chosen as tacky polymer.

Advantageously, a fixing polymer is chosen which has a glass transition temperature (Tg) greater than 25° C.

In accordance with the invention, the relative concentration by weight of fixing polymer in the composition is in general greater than 0.01%, and preferably greater than 0.1%.

A particularly preferred form of the branched sulphonic polyester is that obtained by polymerization of:
(i) at least one difunctional dicarboxylic acid not carrying a sulphonic function;
(ii) at least one difunctional monomer carrying at least one sulphonic function, the functional group(s) being chosen from the group comprising hydroxyl, carboxyl and amino groups;
(iii) at least one diol or a mixture of diol(s) and of diamine(s);
(iv) optionally one difunctional monomer chosen from the group comprising hydroxycarboxylic acids, aminocarboxylic acids and mixtures thereof;
(v) at least one multifunctional reagent carrying at least three functional groups chosen from the group comprising amino, alcohol and carboxylic acid groups.

Such a polymerization may be carried out starting with:
(i) at least one difunctional dicarboxylic acid not carrying a sulphonic function;
(ii) 2 to 15 relative mol % of difunctional monomer carrying at least one sulphonic function;
(iii) at least one diol or a mixture of diol(s) and of diamine(s);
(iv) 0 to 40 relative mol % of the difunctional monomer chosen from the group comprising the hydroxycarboxylic acids, the aminocarboxylic acids and mixtures thereof;
(v) 0.1 to 40 relative mol % of the multifunctional reagent carrying at least three reactive functional groups.

The branched sulphonic polymers preferably contain substantially equal proportions, as number of equivalents, of carboxylic acid functions, on the one hand, and of diol and/or diol and diamine functions, on the other hand.

The difunctional dicarboxylic acid (i) is preferably chosen from the group comprising aliphatic dicarboxylic acids, alicyclic dicarboxylic acids, aromatic dicarboxylic acids or a mixture thereof and more particularly from the group comprising 1,4-cyclohexanedioic acid, succinic acid, glutaric acid, adipic acid, azelaic acid, sebacic acid, fumaric acid, maleic acid, 1,3-cyclohexanedioic acid, phthalic acid, terephthalic acid and isophthalic acid or mixtures thereof.

The difunctional monomer (ii) as defined above is preferably chosen from the group comprising dicarboxylic acids, dicarboxylic acid esters, glycols and hydroxy acids each containing at least one metal sulphonate group.

The diol (iii) is preferably chosen from the group comprising alkanediols and polyalkylenediols and more particularly from the group comprising ethylene glycol, propylene glycol, diethylene glycol, triethylene glycol and polypropylene glycol.

The diamine (iii) may be chosen from the group comprising alkanediamines and polyalkylenediamines.

The multifunctional reagent (v) is preferably chosen from the group comprising trimethylolethane, trimethylolpropane, glycerol, pentaerythritol, sorbitol, trimellitic anhydride, erythritol, threitol, dipentaerythritol, pyromellitic dianhydride and dimethylpropionic acid.

The branched sulphonic polymers more particularly desired by the present invention are those described in patent applications WO 95/18191, WO 97/08261 and WO 97/20899.

In accordance with the invention, there is advantageously chosen, as branched sulphonic polymer, the polymer AQ 1350 marketed by the company Eastman. This polymer AQ 1350 is defined by:
a glass transition temperature, given by the supplier, equal to 0° C.;
a maximum peeling force $F_{max}$ equal to 25 N.

According to a second advantageous embodiment of the compositions in accordance with the invention, (meth)acrylic ester polymer is used as tacky polymer.

The tacky (meth)acrylic ester polymers used in accordance with the invention advantageously comprise:
(a) from 9 to 99% by weight of a (meth)acrylic ester monomer relative to the total weight of the polymer;
(b) up to 90% of comonomer(s);
(c) from 1 to 10% of a vinylidene monomer containing a carboxyl or hydroxyl group.

The (meth)acrylic ester monomer (a) generally corresponds to the formula (I) or (II):

$$CH_2=CH-COOR \quad\quad (I)$$

$$CH_2=C(CH_3)-COOR \quad\quad (II)$$

in which R represents a $C_1$ to $C_{18}$ alkyl, an alkoxy($C_2$ to $C_8$ alkyl), an alkylthio($C_2$ to $C_8$ alkyl) or a $C_2$ to $C_8$ cyanoalkyl. By way of example, the monomer (a) may be chosen from the group comprising methyl acrylate, ethyl acrylate, n-butyl acrylate, isobutyl acrylate, hexyl acrylate, octyl acrylate, 2-ethylhexyl acrylate, decyl acrylate, methoxyacrylate, ethoxyacrylate, methylthiomethyl acrylate and cyanopropyl acrylate.

The comonomer (b) may contain one or more vinylidene groups having terminal $CH_2=C$ groups, such as:
acrylic or methacrylic esters, such as methyl methacrylate, ethyl methacrylate, n-butyl methacrylate, methyl ethacrylate,
vinyl halides such as vinyl chloride;
vinyl and allyl esters such as vinyl acetate, vinyl butyrate, vinyl chloroacetate;
aromatic vinyls such as styrene, vinyltoluene, chloromethylstyrene, vinylnaphthalene; and
vinyl nitriles such as acrylonitrile or methacrylonitrile.
Among the vinylidene monomers containing hydroxyl groups (c), there may be mentioned acrylate monomers containing a terminal hydroxyl group, such as hydroxyethyl acrylate, hydroxyethyl methacrylate, hydroxypropyl acrylate, hydroxypropyl methacrylate, hydroxybutyl acrylate or alternatively certain hydroxymethylated derivatives of diacetone acrylamide, for example N-methylolacrylamide, N-methylolmaleamide, N-propanolacrylamide, N-methylolmethacrylamide, N-methylol-p-vinylbenzamide.

Among the vinylidene monomers containing carboxyl groups (c), there may be mentioned for example acrylic or methacrylic acid, itaconic acid, citraconic acid, maleic acid.

The tacky (meth)acrylic ester polymers particularly desired by the present invention are those described in U.S. Pat. No. 5,234,627 and U.S. Pat. No. 4,007,147.

In accordance with the invention, the polymer Hycar 26 120 marketed by the company Goodrich is advantageously chosen as (meth)acrylic ester polymers. This polymer Hycar 26 120 is defined by:

a glass transition temperature, given by the supplier, equal to −10° C.;

a maximum peeling force $F_{max}$ equal to 6.25 N.

The fixing polymer is generally chosen from anionic, cationic, amphoteric and nonionic fixing polymers and mixtures thereof.

These fixing polymers may be used in solubilized form or alternatively in the form of a dispersion of solid particles of polymer.

As cationic fixing polymer, there is preferably chosen the polymers comprising primary, secondary, tertiary and/or quaternary amine groups which are part of the polymer chain or which are directly attached to it, and having a molecular weight of between 500 and about 5,000,000 and preferably between 1000 and 3,000,000.

As anionic fixing polymers, there are preferred the polymers comprising groups derived from a carboxylic, sulphonic or phosphoric acid and which have a weight-average molecular weight of between about 500 and 5,000,000.

As amphoteric fixing polymers, there are preferably chosen the polymers comprising B and C units randomly distributed in the polymer chain, where B denotes a unit derived from a monomer comprising at least one basic function, in particular a basic nitrogen atom and C denotes a unit derived from an acidic monomer comprising one or more carboxylic or sulphonic groups or alternatively B and C may denote groups derived from zwitterionic monomers of carboxybetaines or sulphobetaines; B and C may also denote a cationic polymer chain comprising primary, secondary, tertiary or quaternary amine groups, in which at least one of the amine groups carries a carboxylic or sulphonic group attached via a hydrocarbon radical; or alternatively B and C are part of a chain of a polymer containing an ethylene-α,β-dicarboxylic unit of which one of the carboxylic groups has been caused to react with a polyamine comprising one or more primary or secondary amine groups.

As nonionic fixing polymers, polyurethanes are advantageously chosen.

Among the fixing polymers used in solubilized form, the polymers chosen from the group comprising silicone-containing acrylic polymers, polymers based on a vinylpyrrolidone and vinylcaprolactam monomer will be preferably used.

Among the fixing polymers which exist in the form of a dispersion, those comprising acrylic or methacrylic monomers and esters thereof or alternatively those comprising styrene monomers will be preferably used.

The composition may be provided in vaporizable, foam, gel or lotion form and the cosmetically acceptable vehicle may consist of an appropriate solvent to which additives such as gelling agents or foaming agents are added. In general, the solvent is chosen from water, alcohols or an aqueous-alcoholic mixture.

The compositions may contain, in addition, an appropriate quantity of propellants such as customary compressed or liquefied gases, preferably compressed air, carbon dioxide or nitrogen, or alternatively a gas which is soluble or otherwise in the composition, such as dimethyl ether, hydrocarbons which are fluorinated or otherwise and mixtures thereof.

The subject of the invention is also an aerosol device consisting of a container containing an aerosol composition consisting, on the one hand, of a liquid phase (or juice) containing at least one composition in accordance with the invention in an appropriate solvent and a propellant as well as a means of distributing the said aerosol composition.

Yet another subject of the invention is a method of treating keratinous fibres, in particular hair, characterized in that the composition in accordance with the invention is applied to the said fibres before or after shaping the hairstyle.

The composition in accordance with the invention is generally used in or for making a cosmetic hairstyling formulation.

The examples below make it possible to illustrate the invention without however seeking to limit the scope thereof. The polymers indicated below will be used:

| | |
|---|---|
| Amphomer | Octylacrylamide/acrylate/butylaminoethyl/methacrylate copolymer marketed by National Starch |
| Polymer LO-21 DRY | Polydimethyl/methyl siloxane containing methyl 3-propylthioacrylate/methyl methacrylate/methacrylic acid groups marketed by 3M |
| Luviskol VA64P | Polyvinylpyrrolidone marketed by BASF |
| Uramul SC 132 | Acrylic copolymer latex marketed by DMS RESINS; Tg = 50° C. |
| AQ 1350 | Branched sulphonic polyester marketed by the company Eastman |

EXAMPLES

Compositions in accordance with the invention comprising a combination of a branched sulphonic polymer and a fixing polymer are compared below with compositions in accordance with the prior art containing either the branched sulphonic polymer alone, or the fixing polymer alone.

Example 1

Comparative

Sensory tests are carried out in order to compare the performance of compositions in accordance with the invention and of compositions in accordance with the prior art. The comparison is made on the retention of the hairstyle over time and under a constraint.

For that, 3 compositions in accordance with the invention and 4 compositions in accordance with the prior art are made. These compositions are applied to wigs of natural hair. Next, the shape retention of the wig and the return of the shape of the wigs after shaking are evaluated.

| | |
|---|---:|
| Composition 1 (invention): | |
| AQ 1350 | 4 g |
| Amphomer | 2 g |
| Water | 75 g |
| 2-Amino-2-methyl-1-propanol qs neutralization Amphomer | 0.37 g |
| Alcohol    qs | 100 g |
| Composition 2 (invention): | |
| AQ 1350 | 4 g |
| Polymer LO-21 DRY previously 90% neutralized | 2 g |
| Water | 75 g |
| Alcohol    qs | 100 g |
| Composition 3 (invention): | |
| AQ 1350 | 4 g |
| LUVISKOL VA 64 P | 2 g |
| Water | 75 g |
| Alcohol    qs | 100 g |
| Composition 4 (prior art - branched sulphonic polyester alone): | |
| AQ 1350 | 6 g |
| Water | 75 g |

-continued

| | |
|---|---|
| Alcohol qs | 100 g |
| Composition 5 (prior art - fixing polymer alone): | |
| Amphomer | 6 g |
| Water | 75 g |
| 2-Amino-2-methyl-1-propanol qs neutralization Amphomer | 1.09 g |
| Alcohol qs | 100 g |
| Composition 6 (prior art - fixing polymer alone): | |
| Polymer LO-21 DRY previously 90% neutralized | 6 g |
| Water | 75 g |
| Alcohol qs | 100 g |
| Composition 7 (prior art - fixing polymer alone): | |
| LUVISKOL VA 64 P | 6 g |
| Water | 75 g |
| Alcohol qs | 100 g |

Each of the compositions is introduced into a pump dispenser. 3 grams of each composition are sprayed onto a wig of hair 20 cm long previously shampooed and drained. It is allowed to dry for 4 hours and the wig is turned over.

The wig is shaken by means of an alternating rotation for 2 hours. The final shape of the locks is compared with the shape which they had before shaking and the shape retention is estimated. A score from 0 to 5 is used:

0 indicates a very poor shape retention and a completely collapsed hairstyle, 5 indicates an excellent retention and a hairstyle which has remained intact and voluminous in spite of the shaking.

The wigs are then disentangled and they are again shaken for 20 seconds. The return of the shape of the hairstyle when it has been subjected to all these operations is estimated. The same score scale ranging from 0 to 5 is used.

Table 1 summarizes the results.

TABLE 1

| Composition | Shape retention after shaking | Return of the shape after shaking and disentanglement |
|---|---|---|
| 1 | 3.25 | 2.5 |
| 2 | 4.0 | 4.0 |
| 3 | 4.5 | 4.25 |
| 4 | 2.0 | 4.0 |
| 5 | 3.75 | 0.75 |
| 6 | 3.5 | 1.0 |
| 7 | 2.0 | 0.75 |
| without treatment | 0 | 0.5 |

Table 1 shows that the compositions in accordance with the invention and comprising the combination of polymers offer better results in terms of shape retention after shaking and of a return of the shape after shaking and disentanglement than the compositions in accordance with the prior art.

Example 2

A composition 8 in accordance with the invention is prepared and the retention of the hairstyle as well as certain cosmetic properties are estimated.

Composition 8 (Invention):

| | |
|---|---|
| AQ 1350 | 4 g |
| URAMUL SC 132 | 0.5 g |
| Water qs | 100 g |

A wig of 20 g of natural hair is taken and 2.5 grams of composition 8 are applied to the hair and allowed to dry.

It is observed that the hair is maintained very well. Disentanglement is easy and the locks have a good feel after disentanglement.

The invention claimed is:

1. A cosmetic composition for keratinous fibers comprising, in a cosmetically acceptable medium, at least one tacky polymer having a glass transition temperature (Tg) of less than 20° C. and at least one fixing polymer having a glass transition temperature (Tg) greater than 15° C.

2. A composition according to claim 1, wherein said at least one tacky polymer has a peeling profile defined by at least a maximum peeling force $F_{max}$>3 Newtons.

3. A composition according to claim 2, wherein said at least one tacky polymer has a peeling profile defined by at least a maximum peeling force $F_{max}$>5 Newtons.

4. A composition according to claim 1, wherein said keratinous fibers are chosen from hair.

5. A composition according to claim 2, wherein when said glass transition temperature of said at least one tacky polymer is less than −15° C., and wherein said peeling profile is further defined by at least an energy for separation $E_{s(M/V)}$ of less than 300 µJ.

6. A composition according to claim 3, wherein when said glass transition temperature of said at least one tacky polymer is less than −15° C. and wherein said peeling profile is further defined by at least an energy for separation $E_{(m/V)}$ of less than 300 µJ.

7. A composition according to claim 1, wherein said at least one tacky, polymer is chosen from branched sulfonic polyester polymers and (meth)acrylic ester polymers.

8. A composition according to claim 1, wherein said at least one tacky polymer is present in an amount greater than 0.01% by weight relative to the total weight of the composition.

9. A composition according to claim 8, wherein said at least one tacky polymer is present in an amount greater than 0.1% by weight relative to the total weight of the composition.

10. A composition according to claim 9, wherein said at least one tacky polymer is present in an amount greater than 0.5% by weight relative to the total weight of the composition.

11. A composition according to claim 1, wherein said at least one fixing polymer has a glass transition temperature (Tg) greater than 25° C.

12. A composition according to claim 1, wherein said at least one fixing polymer is present in an amount greater than 0.01% by weight relative to the total weight of the composition.

13. A composition according to claim 12, wherein said at least one fixing polymer is present in an amount greater than 0.1% by weight relative to the total weight of the composition.

14. A composition according to claim 7, wherein said branched sulfonic polyester polymers are formed from: (i) at least one dicarboxylic acid carrying two functional groups, wherein said functional groups are chosen from functional groups other than sulfonic groups:

(ii) at least one sulfomonomer comprising at least one sulfonic group and carrying two functional groups, wherein said functional groups are chosen from hydroxyl groups, carboxyl groups and amino groups;

(iii) at least one diol and optionally at least one diamine;

(iv) optionally at least one monomer carrying two functional groups, wherein said at least one monomer is chosen from hydroxycarboxylic acids, and aminocarboxylic acids; and (v) at least one compound carrying at least three functional groups chosen from amino groups, alcohol groups, and carboxylic acid groups.

15. A composition according to claim 14, wherein said branched sulfonic polyester polymers are formed from:
(i) said at least one dicarboxylic acid carrying two functional groups, wherein said functional groups are chosen from functional groups other than sulfonic groups;
(ii) 2 to 15 relative mol % of said at least one sulfomonomer comprising at least one sulfonic group and carrying two functional groups, wherein said functional groups are chosen from hydroxyl groups, carboxyl groups and amino groups;
(iii) said at least one diol and optionally said at least one diamine;
(iv) 0 to 40 relative mol % of said at least one monomer carrying two functional groups, wherein said at least one monomer is chosen from hydroxycarboxylic acids, and aminocarboxylic acids; and
(v) 0.1 to 40 relative mol % of said at least one compound carrying at least three functional groups chosen from amino groups, alcohol groups, and carboxylic acid groups.

16. A composition according to claim 14, wherein said carboxylic acid functions are present in a total number equal to a total number of said diol and said optional diamine functions combined.

17. A composition according to claim 14, wherein said at least one dicarboxylic acid carrying two functional groups (i) is chosen from aliphatic dicarboxylic acids, alicyclic dicarboxylic acids, and aromatic dicarboxylic acids.

18. A composition according to claim 14, wherein said at least one dicarboxylic acid carrying two functional groups (i) is chosen from 1,4-cyclohexanedioic acid, succinic acid, glutaric acid, adipic acid, azelaic acid, sebacic acid, fumaric acid, maleic acid, 1,3-cyclohexanedioic acid, phthalic acid, terephthalic acid, and isophthalic acid.

19. A composition according to claim 14, wherein said at least one sulfomonomer comprising at least one sulfonic group and carrying two functional groups (ii) is chosen from dicarboxylic acids comprising at least one metal sulfonate group, dicarboxylic acid esters comprising at least one metal sulfonate group, glycols comprising at least one metal suffocate group, and hydroxy acids comprising at least one metal sulfonate group.

20. A composition according to claim 14, wherein said at least one dial of (iii) is chosen from alkanediols and polyalkylene dials.

21. A composition according to claim 14, wherein said at least one dial of (iii) is chosen from ethylene glycol, propylene glycol, diethylene glycol, triethylene glycol, and polypropylene glycol.

22. A composition according to claim 14, wherein said at least one diamine of (iii) is chosen from alkanediamines and polyalkylenediamines.

23. A composition according claim 14, wherein said at least one compound carrying at least three functional groups chosen from amino groups, alcohol groups, and carboxylic acid groups (v) is chosen from trimethylolethane, trimethylolpropane, glycerol, pentaerythritol, sorbitol, trimellitic anhydride, erythritol, threitol, dipentaerythritol, pyromellitic dianhydride, and dimethylpropionic acid.

24. A composition according to claim 7, wherein said (meth)acrylic ester polymers comprise:
(a) from 9 to 99% by weight of at least one (meth)acrylic ester monomeric unit relative to the total weight of the polymer:
(b) up to 90% of at least one comonomeric unit; and
(c) from 1 to 10% of at least one vinylidene monomeric unit comprising at least one functional group chosen from carboxyl groups and hydroxyl groups.

25. A composition according to claim 24, wherein said at least one (meth)acrylic ester monomeric unit (a) is chosen from monomeric units derived from at least one monomer of formulae (I) and (II):

wherein R is chosen from $C_1$ to $C_{18}$ alkyl groups, alkoxy ($C_2$ to $C_8$ alkyl) groups, alkylthio($C_2$ to $C_8$ alkyl) groups, and $C_2$ to $C_8$ cyanoalkyl groups.

26. A composition according to claim 24, wherein said at least one (meth)acrylic ester monomeric unit (a) is derived from at least one monomer chosen from methyl acrylate, ethyl acrylate, n-butyl acrylate, isobutyl acrylate, hexyl acrylate, octyl acrylate, 2-ethylhexyl acrylate, decyl acrylate, methoxyacrylate, ethoxyacrylate, methylthiomethyl acrylate and cyanopropyl acrylate.

27. A composition according to claim 24, wherein said at least one comonomeric unit (b) comprises at least one vinylidene group comprising terminal $CH_2=C-$ groups.

28. A composition according to claim 27, wherein said at least one comonomeric unit (b) is derived from at least one monomer chosen from:
acrylic esters,
methacrylic esters,
vinyl halides,
vinyl esters,
allyl esters,
aromatic vinyls, and
vinyl nitrites.

29. A composition according to claim 28, wherein said acrylic esters and said methacrylic esters are chosen from methyl methacrylate, ethyl methacrylate, n-butyl methacrylate, and methyl ethacrylate.

30. A composition according to claim 28, wherein said vinyl halides are chosen from vinyl chloride.

31. A composition according to claim 28, wherein said vinyl esters are chosen from vinyl acetate, vinyl butyrate, and vinyl chloroacetate.

32. A process for manufacturing a cosmetic hairstyling formulation comprising including in said cosmetic hairstyling formulation at least one tacky polymer having a glass transition temperature (Tg) of less than 20° C. and at least one fixing polymer having a glass transition temperature (Tg) greater than 15° C.

33. A composition according to claim 28, wherein said aromatic vinyls are chosen from styrene, vinyltoluene, chloromethylstyrene, and vinylnaphthalene.

34. A composition according to claim 28, wherein said vinyl nitrites are chosen from acrylonitrile and methacrylonitrile.

35. A composition according to claim 24, wherein said at least one vinylidene monomeric unit (c) comprises at least one hydroxyl group.

36. A composition according to claim 35, wherein said at least one vinylidene monomeric unit (c) is derived from at least one acrylate monomer comprising a terminal hydroxyl group.

37. A composition according to claim 36, wherein said at least one vinylidene monomeric unit (c) is derived from hydroxyethyl acrylate, hydroxyethyl methacrylate, hydroxypropyl acrylate, hydroxypropyl methacrylate, hydroxybutyl acrylate, and hydroxymethylated derivatives of diacetone acrylamide.

38. A composition according to claim 37, wherein said hydroxymethylated derivatives of diacetone acrylamide are chosen from N-methylolacrylamide, N-methylolmaleamide, N-propanolacrylamide, N-methylolmethacrylamide, and N-methylol-p-vinylbenzamide.

39. A composition according to claim 24, wherein said at least one vinylidene monomeric unit (c) comprises at least one carboxyl group.

40. A composition according to claim 39, wherein said at least one vinylidene monomeric unit (c) is derived from at least one monomer chosen from acrylic acid, methacrylic acid, itaconic acid, citraconic acid, and maleic acid.

41. A composition according to claim 1, wherein said at least one fixing polymer of said composition is chosen from anionic, cationic, amphoteric, and nonionic fixing polymers.

42. A composition according to claim 1, wherein said at least one fixing polymer is either solubilized in said composition or dispersed in said composition.

43. A composition according to claim 42, wherein said cationic fixing polymers are chosen from polymers with a weight-average molecular weight ranging from 500 to 5,000,000 and comprising at least one amine group chosen from primary, secondary, tertiary and quaternary amine groups, wherein said amine groups are part of the polymer chain or are directly attached to the polymer chain.

44. A composition according to claim 43, wherein said cationic fixing polymers have a weight-average molecular weight ranging from 1000 to 3,000,000.

45. A composition according to claim 41, wherein said anionic fixing polymers are chosen from polymers comprising at least one group derived from carboxylic acids, sulfonic acid, and phosphoric acid and having a weight-average molecular weight ranging from 500 to 5,000,000.

46. A composition according to claim 41, wherein said amphoteric fixing polymers are chosen from:
(1) polymers comprising at least one unit B and at least one unit C randomly distributed in the polymer chain of said polymers, wherein said at least one unit B is chosen from monomeric units derived from at least one monomer comprising at least one basic functional group, and wherein said at least one unit C is chosen from monomeric units derived from at least one acidic monomer comprising at least one group chosen from carboxylic groups and sulfonic groups,
(2) polymers comprising at least one unit B and at least one unit C randomly distributed in the polymer chain of said polymers, wherein said at least one unit B and said at feast one unit C are each chosen from monomeric units derived from at least one zwitterionic monomer chosen from zwitterionic monomers of carboxybetaines and zwitterionic monomers of sulfabetaines,
(3) polymers comprising a cationic polymer chain formed from at least one unit B and at least one unit C, wherein said cationic polymer chain comprises at least one amine group chosen from primary, secondary, tertiary, and quaternary amine groups, wherein at least one of said at least one amine group carries a group chosen from carboxylic groups and sulfonic groups, wherein said carried group is attached by way of a hydrocarbon linker, and
(4) polymers comprising at least one ethylene-α,β-dicarboxylic unit wherein one of said two carboxylic groups has been caused to react with at least one polyamine comprising at least one amine group chosen from primary and secondary amine groups.

47. A composition according to claim 46, wherein, when said at least one unit B in (1) is chosen from monomeric units derived from at least one monomer comprising at least one basic functional group, said at least one basic functional group being a basic nitrogen atom.

48. A composition according to claim 41, wherein said nonionic fixing polymers are chosen from polyurethanes.

49. A composition according to claim 1, wherein said at least one fixing polymer is a soluble polymer.

50. A composition according to claim 49, wherein said soluble polymer is chosen from silicone-containing acrylic polymers, polymers formed from at least one vinylpyrrolidone monomer, and polymers formed from at least one vinylcaprolactam monomer.

51. A composition according to claim 1, wherein said at least one fixing polymer is dispersed in said composition and is chosen from polymers formed from at least one acrylic monomer, polymers formed from at least one acrylic ester monomer, polymers formed from at least one methacrylic monomer, polymers formed from at least one methacrylic ester monomer, and polymers formed from at least one styrene monomer.

52. A vaporizable composition, a foam, a gel or a lotion comprising a cosmetic composition for keratinous fibers, which comprises, in a cosmetically acceptable medium, at least one tacky polymer having a glass transition temperature (Tg) of less than 20° C. and at least one fixing polymer having a glass transition temperature (Tg) greater than 15° C.

53. A composition according to claim 1, wherein said cosmetically acceptable medium comprises at least one solvent chosen from water and alcohols.

54. A composition according to claim 1 further comprising at least one additive chosen from gelling agents and foaming agents.

55. A composition according to claim 1 further comprising at least one propellant.

56. A composition according to claim 55, wherein said at least one propellant is chosen from compressed gases, and liquefied gases.

57. A composition according to claim 55, wherein said at least one propellant is chosen from gases.

58. A composition according to claim 55, wherein said at least one propellant is chosen from gases which are soluble in said composition.

59. A composition according to claim 56, wherein said compressed gases and liquified gases are chosen from compressed air, carbon dioxide, and nitrogen.

60. A composition according to claim 58, wherein said gases which are soluble in said composition are chosen from dimethyl ether and fluorinated hydrocarbons.

61. An aerosol device comprising (1) a compartment comprising an aerosol composition comprising a liquid phase and at least one propellant, wherein said liquid phase comprises, in an appropriate solvent, a cosmetic composition for keratinous fibers comprising, in a cosmetically acceptable medium, at least one tacky polymer having a glass transition temperature (Tg) of less than 20° C. and at least one fixing polymer having a glass transition temperature (Tg) greater than 15° C., and (2) a member for distributing said aerosol composition.

62. A process of treating keratinous fibers comprising applying to said fibers, before and/or after shaping a hairstyle, a cosmetic composition for keratinous fibers comprising, in a cosmetically acceptable medium, at least one tacky polymer having a glass transition temperature (Tg) of less than 20° C. and at least one fixing polymer having a glass transition temperature (Tg) greater than 15° C.

63. A process according to claim 62, wherein said keratinous fibers are chosen from hair.

64. A composition according to claim 2, wherein said maximum peeling force $F_{max}$ is measured with an extensometer and is a maximum tensile force for peeling apart 38 mm² coated surfaces of two rigid, inert, and nonabsorbent supports (A) and (B) placed opposite each other, wherein said surfaces have been (1) coated with a tacky polymer dissolved at 5% in a solvent, at the rate of 1 mg/mm², (2) dried for 24 hours at 22° C. under a relative humidity of 50%, (3) compressed for 20 seconds under a force of 3 Newtons, and (4) pulled apart for 30 seconds at a rate of 20 mm/min.

65. A composition according to claim 64, wherein said solvent is chosen from aqueous solvents, aqueous-alcoholic solvents, and alcoholic solvents.

66. A composition according to claim 64, wherein said supports (A) and (B) are chosen from polyethylene supports, polypropylene supports, metal alloy supports, and glass supports.

67. A composition according to claim 5, wherein said $E_{s(M/V)}$ is an amount of energy provided by an extensometer for peeling apart 38 mm² coated surfaces of two rigid, inert, and nonabsorbent supports (C) and (D) placed opposite each other, wherein one of said two supports comprises cut glass and a second of said two supports is chosen from polyethylene supports, polypropylene supports, metal alloy supports, and glass supports, and wherein said surfaces have been (1) coated with a tacky polymer dissolved at 5% in a solvent, at the rate of 1 mg/mm², (2) dried for 24 hours at 22° C. under a relative humidity of 50%, (3) compressed for 20 seconds under a force of 3 Newtons, and (4) pulled apart for 30 seconds at a rate of 20 mm/min.

68. A composition according to claim 67, wherein said solvent is chosen from aqueous solvents, aqueous-alcoholic solvents, and alcoholic solvents.

69. A composition according to claim 67, wherein said $E_{s(M/V)}$ is an amount of energy calculated by means of the following formula:

$$\int_{X_{s1}+0.05}^{X_{s2}} F(x)dx$$

where F(x) is a force necessary to produce a movement (x), $x_{s1}$ is the movement in millimeters produced by a maximum tensile force, and $x_{s2}$ is the movement in millimeters produced by a tensile force sufficient to completely separate said surfaces of said supports (C) and (D).

* * * * *

UNITED STATES PATENT AND TRADEMARK OFFICE
CERTIFICATE OF CORRECTION

PATENT NO. : 7,740,832 B1 Page 1 of 1
APPLICATION NO. : 09/719101
DATED : June 22, 2010
INVENTOR(S) : Isabelle Rollat-Corvol et al.

It is certified that error appears in the above-identified patent and that said Letters Patent is hereby corrected as shown below:

Claim 46, column 11, line 51, "feast" should read --least--.

Signed and Sealed this

Fifth Day of October, 2010

David J. Kappos
*Director of the United States Patent and Trademark Office*